United States Patent
Zhou et al.

(10) Patent No.: US 6,903,141 B2
(45) Date of Patent: Jun. 7, 2005

(54) SLURRY-PHASE SKELETAL IRON CATALYST PROCESS FOR SYNTHESIS GAS CONVERSION TO HYDROCARBONS

(75) Inventors: Peizheng Zhou, Lawrenceville, NJ (US); Larry Abrams, Cherry Hill, NJ (US); Christine Marie Long, Princeton, NJ (US); Lu Yijun, Lawrenceville, NJ (US)

(73) Assignee: Hydrocarbon Technologies, Inc., Lawrenceville, NJ (US)

( * ) Notice: Subject to any disclaimer, the term of this patent is extended or adjusted under 35 U.S.C. 154(b) by 253 days.

(21) Appl. No.: 10/267,236

(22) Filed: Oct. 8, 2002

(65) Prior Publication Data

US 2003/0109591 A1 Jun. 12, 2003

Related U.S. Application Data

(63) Continuation-in-part of application No. 10/107,915, filed on Mar. 27, 2002, now Pat. No. 6,777,452, which is a continuation-in-part of application No. 09/895,621, filed on Jul. 2, 2001, now abandoned, which is a continuation of application No. 09/399,852, filed on Sep. 21, 1999, now Pat. No. 6,277,895.

(51) Int. Cl.[7] .............................................. C07C 27/00
(52) U.S. Cl. ...................... 518/719; 518/700; 518/715; 518/720
(58) Field of Search ................................ 518/700, 709, 518/715, 719, 720

(56) References Cited

U.S. PATENT DOCUMENTS 6,068,760 A * 5/2000 Benham et al. ............. 518/700
6,156,809 A * 12/2000 Clark et al. ................. 518/719

OTHER PUBLICATIONS

Zhou P.Z. , 'Fischer–Tropsch slurry reactor catalyst/wax separation techniques', U.S. Department of Energy Technology Center Feb. 1991.*

* cited by examiner

Primary Examiner—J. Parsa
(74) Attorney, Agent, or Firm—Workman Nydegger (57) ABSTRACT

A continuous process is disclosed for the production of hydrocarbon liquids and wax by Fischer-Tropsch conversion of synthesis gas in contact with promoted skeletal iron catalyst particles in a slurry reactor. Wax product is readily separated from the skeletal iron catalyst in a catalyst settling drum and concentrated catalyst particles in wax slurry are recycled from the settling drum to the slurry reactor, while essentially solid-free wax is recovered as a product.

20 Claims, 1 Drawing Sheet

Figure
Process Flow Diagram

Figure
Process Flow Diagram

SLURRY-PHASE SKELETAL IRON CATALYST PROCESS FOR SYNTHESIS GAS CONVERSION TO HYDROCARBONS

REFERENCE TO RELATED APPLICATIONS

This application is a continuation-in-part of U.S. patent application Ser. No. 10/107,915 filed Mar. 27, 2002, now U.S. Pat. No. 6,777,459, which is a continuation-in-part of U.S. patent application Ser. No. 09/895,621, filed Jul. 2, 2001, now abandoned which is a continuation of U.S. patent application Ser. No. 09/399,852, filed Sep. 21, 1999, now U.S. Pat. No. 6,277,895.

FIELD OF THE INVENTION

This invention relates to a process for the conversion of fossil fuels to liquid and gaseous hydrocarbons. The invention particularly relates to an integrated process for the conversion of fossil fuels to synthesis gas followed by the conversion of the synthesis gas to mainly fuel, wax and chemical grade straight chain liquid hydrocarbons. The synthesis gas conversion is carried out in a vessel containing a slurry-phase reactor bed comprising preferably a saturated liquid hydrocarbon medium in which fine particles of promoted or unpromoted skeletal iron catalyst are suspended. Essentially, solids-free wax product is readily separated and recovered.

BACKGROUND OF THE INVENTION

The conversion of fossil fuels such as coal, natural gas and petroleum coke to liquid hydrocarbon fuels and/or chemicals has been the subject of intensive research and development throughout the industrialized world for many years to provide a practical alternative to petroleum crude oil production and open-up the world's vast reserves of coal as a competitive source for essential hydrocarbons. Many processes have been developed for the direct or indirect catalytic hydrogenation of fossil fuels to yield liquid hydrocarbons; some large pilot plants have been built and operated, and about twenty commercial scale plants have been built for the conversion of coal to primarily liquid hydrocarbons. Of these twenty plants, most were built by the German government during World War II. About half of them were built using the well-known Fischer-Tropsch process for converting synthesis gas to liquid hydrocarbons in contact with iron catalyst and, operationally at least, worked well enough for war-time needs. Subsequently, the South African Government (SASOL, Ltd) built commercial size coal conversion plants to produce hydrocarbon fuels and chemicals which also were successfully based on indirect conversion using Fischer-Tropsch chemistry and iron catalysis.

From an operational point of view, the commercial liquefaction of coal or natural gas based on indirect Fischer-Tropsch (F-T) chemistry has been demonstrated to be an engineering success. However, true economic success has so far eluded the developers of direct or indirect coal or natural gas liquefaction processes, largely because of the low cost of crude oil as the competitive alternative but also because of the high cost of the direct or indirect liquefaction conversion step where process economic performance is so dependent on feed price, catalyst cost, activity, resistance to attrition and other challenges which must be overcome or ameliorated by cost-enhancing process modifications. There is a genuine potential for indirect coal or natural gas liquefaction via Fisher-Tropsch (F-T) chemistry to substantially narrow the competitive gap between that process and crude oil. A key to that potential is improvement in the chemistry of catalysis as applied to the Fischer-Tropsch process for synthesis gas conversion to hydrocarbons.

A known, practical method for preparing liquid hydrocarbons rich in valuable 1-olefins is to convert a fossil fuel, especially natural gas, to synthesis gas, i.e., a mixture of carbon monoxide and hydrogen, by steam reforming of natural gas followed by conversion of the synthesis gas to liquid hydrocarbons over a precipitated iron F-T catalyst. However, most precipitated iron catalysts in the F-T process are especially fragile and break down easily in slurry-phase reactors into very fine particles under conventional reaction conditions. A significant portion of the hydrocarbon products comprise waxy hydrocarbons and these waxy materials become mixed with sub-micron size iron catalyst particles forming the slurry to the extent that separation of the very fine catalyst particles from the entraining waxy product of the F-T process is extremely difficult. Costly and comparably complicated separation processes must be resorted to in the conventional F-T process to effect the separation of the fine precipitated iron catalyst particle carry-over from the wax product of the F-T process. The result is a substantial loss of recyclicable precipitated iron catalyst particles coupled with an added cost burden on the F-T process economics from the additional cost of replacing lost catalyst and the more elaborate process steps used to try to separate fine catalyst particles from wax products. Catalyst/wax separation difficulties have been a major barrier for precipitated iron catalysts to be successfully applied in commercial operation.

In applicants' U.S. Pat. Nos. 6,265,451 and 6,277,895, incorporated herein by reference in their entirety, skeletal iron F-T catalysts are taught for the production of liquid hydrocarbons in a slurry reactor from fossil-fuel derived synthesis gas. The patents teach and claim a relatively simple and inexpensive method for preparing the skeletal iron F-T catalyst that experiences less attrition, easy catalyst/wax separation, and the conversion of syngas is higher than that obtained by using fused iron as catalyst. Also, the conversion of the feed is equivalent to that achieved by precipitated iron F-T catalysts. Product selectivity favors the production of distillate hydrocarbons and less wax.

Now, the applicants herein come forward with the discovery of a fully integrated process that successfully utilizes the many advantages of the foregoing skeletal iron F-T catalyst in a slurry bed reactor and overcomes the major process limitations experienced heretofore in the production of liquid hydrocarbons from synthetic gas from fossil fuels such as natural gas and coal.

SUMMARY OF THE INVENTION

This invention provides a continuous process for the conversion of synthesis gas into hydrocarbon liquids by contacting a feedsteam comprising synthesis gas with saturated hydrocarbon liquid and suspended skeletal iron catalyst particles in a slurry-bed reactor under conditions sufficient to convert the synthesis gas feedstream into by-product gases, light $C_1$–$C_4$ hydrocarbon gases and $C_5$+ hydrocarbon liquids including hydrocarbon wax. The by-product gases, light hydrocarbon gases and $C_5$+ hydrocarbon liquids, excluding wax, are separated as a reactor vapor overhead stream for separation and recovery of $C_5$+ hydrocarbon liquid products, primarily by fractionation of the liquid products. A reactor liquid slurry stream is removed from the main body of the reactor bed and passed into a catalyst settling drum by a reactor overflow line wherein the skeletal iron catalyst particles in the overflow stream concentrate in a bottom portion of the drum as essentially intact particles mixed with a minimal quantity of hydrocarbon wax. A hydroclone can also be used before the slurry stream entering the catalyst settling drum to enhance and expedite catalyst/wax separation. A catalyst settling drum side draw stream essentially free of catalyst particles is withdrawn from an upper portion of the drum and wax product is recovered there from. A catalyst settling drum bottom stream rich in equilibrium skeletal iron catalyst particles concentrated in a wax slurry is passed into a bottom portion of the reactor as a skeletal iron catalyst recycle stream. A net purge is taken from the catalyst recycle stream to remove catalyst of reduced activity which is replaced by an equivalent amount of fresh catalyst.

The reactor of the invention comprises a slurry bed reactor containing the skeletal iron catalyst particles and internal cooling coils with the liquid level in the reactor maintained above the top of the cooling coils by the liquid overflow line.

Reactor conditions include a temperature of 230° C. to 280° C., pressure of 1.7 to 5.5 MPa, and space velocity of 1–5 L/g-cat/hr.

The product wax is recovered from a catalyst settling drum fed by a side draw stream from the reactor. Wax product is removed from the side of the catalyst settling drum and pumped through a filter to remove any traces of entrained spent catalyst. The filtered stream is passed to a wax product flash drum; and wax product is recovered from a bottom portion of the flash drum.

Skeletal iron catalyst is recycled to the reactor from the bottom of the catalyst settling drum by pumping the recycle stream to a position in the reactor below the reactor cooling coils. The operating conditions of the catalyst settling drum is preferably about a temperature of 230–270° C., pressure of 1.5–5.0 MPa Abs, and residence time@HHL of 15–60 min.

The skeletal iron catalyst employed in the invention is preferably an activated promoted catalyst, although a skeletal iron catalyst that does not contain catalyst promoting metals can be used. The catalyst is activated prior to incorporating into the process by heating in contact with hydrogen and/or nitrogen gas.

The preferably promoted skeletal iron catalysts contain 50–90 wt % iron, 0–5.0 wt % copper, 0.1–5.0 wt % manganese, and 0.1–3.0 wt % potassium with the remainder being aluminum. The catalyst has good particle strength and provides high catalytic activity and selectivity towards the formation of desirable hydrocarbon products from the CO and $H_2$ feedstreams, particularly liquid transportation fuels and alpha olefins.

The promoted skeletal iron catalysts of this invention are prepared utilizing improved method steps, which include mixing together iron chips or powder with the non-ferrous metal chips or powders of aluminum, copper and manganese, heating and melting the metal chips mixture to form a molten metal alloy, then rapidly cooling the molten metal alloy to room temperature (15–20° C.) such as by quenching in water, and then pulverizing the resulting solid metal alloy to provide fine precursor iron alloy particles having size range of 0.1–10 mm (10–10,000 microns). A major portion of the aluminum is removed by extracting/leaching by contacting with a suitable caustic solution such as NaOH or KOH to provide base iron catalyst particles. The base catalyst particles are next impregnated or loaded with the potassium promoter to provide 0.1–3.0 wt. % potassium. Because the spent catalyst particles are readily separable from the hydrocarbon product liquids by gravity sedimentation, the skeletal iron catalyst is especially suitable for use in slurry-phase type reactors for Fischer Tropsch synthesis processes.

DETAILED DESCRIPTION OF THE INVENTION

The Continuous Process Including Wax Separation

Figure 1:
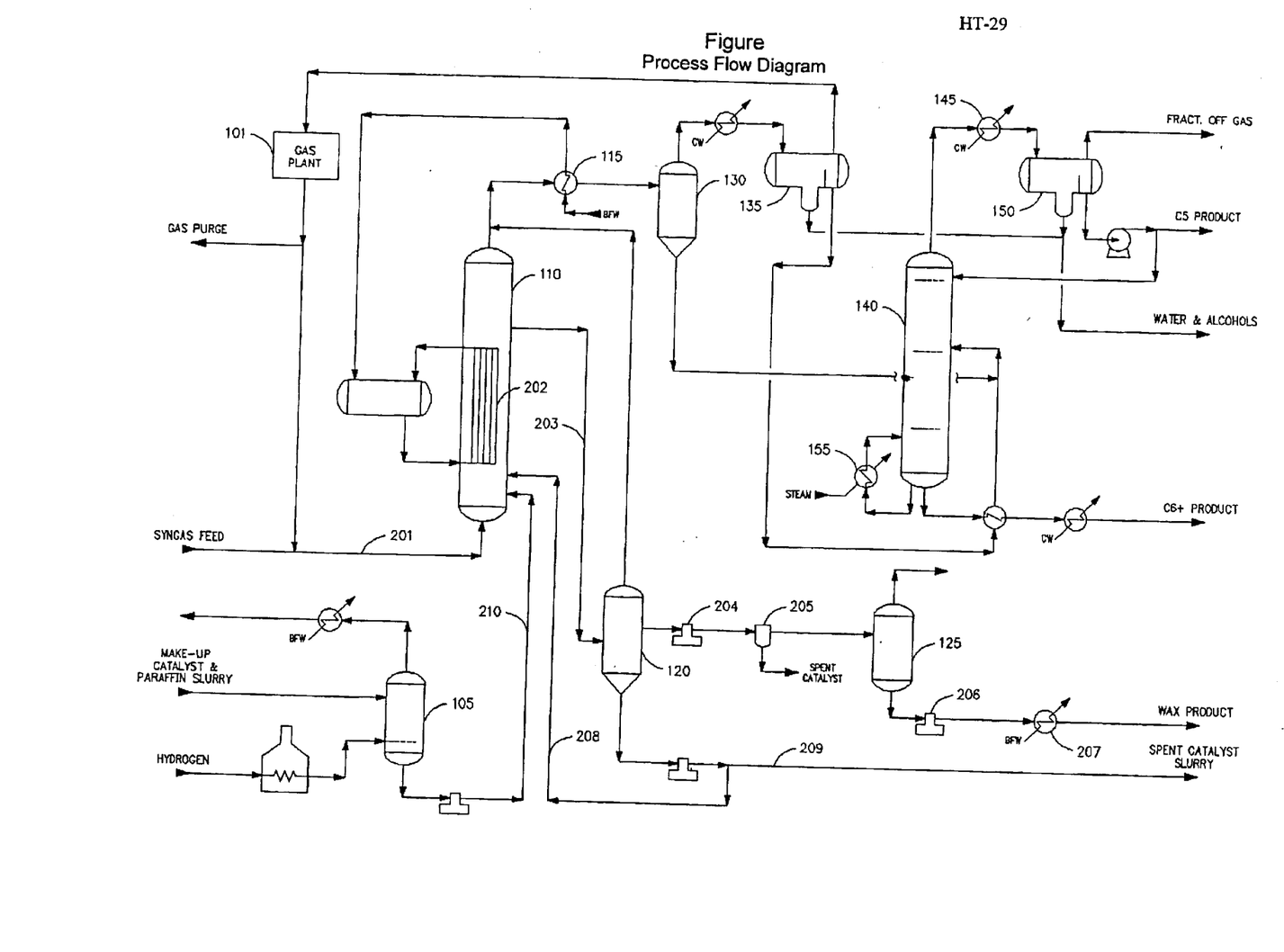
The FIGURE is a detailed process flow diagram depicting a preferred, once through, continuous process of the invention utilizing promoted or unpromoted skeletal iron catalyst in a slurry phase Fischer-Tropsch reactor for the conversion of synthesis gas to liquid hydrocarbons and wax. The preferred embodiment of the process of the invention can be carried out in either the depicted 'once through' mode or in a 'recycle' mode.

Referring to the FIGURE, a preferred, once through process of the invention is illustrated, preferably employing promoted skeletal iron catalyst in a slurry phase reactor. The process may be carried out preferably as a once through process or unreacted components of syngas may be recovered and recycled to the reactor. The major components of an on-stream, once through process of the invention include: a gas plant (101), a catalyst activation vessel (105), Fischer-Tropsch reactor (110), heat exchanger (115), catalyst settling vessel (120), wax product flash vessel (125), warm and cold reactor effluent flash drums (130) and (135), product fractionator (140) with fractionator condenser (145) and reflux drum (150) with reboiler (155).

For the process of the invention, syngas is generated (not shown in the FIGURE) in an upstream reforming or coal gasification unit which converts natural gas or coal into syngas. The syngas is cleaned to be essentially free of sulfur and oxygen and sent (201) to the reactor (110) as feed gas under flow control through a bottom sparger. The gas flow keeps the liquid-catalyst slurry of skeletal iron particles in suspension while the syngas is converted into light gases and full boiling range liquid components. Heat generated by the reaction is removed by internal cooling coils (202) where boiler feed water is circulated to the coils and steam is generated.

Liquid level in the reactor is maintained above the top level of the cooling coils (202) by a slurry overflow line (203) which flows to the catalyst settling drum (120). In the catalyst settling drum (120) the bulk of the catalyst in the reactor overflow settles to the bottom of the drum (120) while an overhead liquid containing only a small amount of catalyst fines rises to the top section of the drum (120). Entrained and dissolved gases leave the top of the catalyst settling drum and join the vapors leaving the reactor. Over 95 weight percent of the suspended catalyst particles in the reactor overflow stream that is passed to the settling drum settle in the bottom portion of the catalyst settling drum. A liquid stream containing minimal solid catalyst is removed from the upper side portion of the drum and pumped (204) under level control through filter (205) where the small amount of entrained catalyst is removed. The clear filtrate is sent to the wax product flash drum (125). After venting gases from drum (125), the clear wax product liquid is pumped (206) and cooled (207) to recover the wax product as a liquid.

The reactor slurry overflow via line (203) may pass through a hydroclone (not shown) before entering the catalyst settling drum (120) to enhance and expedite catalyst/wax separation.

The bulk of the concentrated slurry from the bottom of the catalyst settling drum (120) is returned (208) by pumping to the reactor (110). This liquid is concentrated with respect to catalyst particles. A small amount of this slurry is purged (209) under flow control. The rate at which slurry is returned from the settling drum (120) to the reactor (110) controls the rate of overflow slurry from the reactor to the catalyst settling drum. The level controller on the drum (120) fixes the liquid level both in the catalyst settling drum and in the reactor (110). The catalyst settling drum is elevated so that its high liquid level is just above the level of the top of the bank of the reactor cooling coils (202).

Wax is withdrawn from the reactor on a continuous basis and flows by gravity to the slurry settling drum, i.e., the catalyst settling drum. The catalyst settles out of the wax slurry and concentrates in the bottom of the settling drum. The clear wax product is withdrawn from the slurry settling drum sidedraw and contains less than 0.2 wt % catalyst solids. The settling drum bottoms stream contains about 40 wt % solids which are recycled back to the reactor. The performance and preferred operating conditions for the slurry settling drum are summarized as follows:

| Conditions | Slurry Settling Drum (120) |
|---|---|
| Orientation | vertical/elevated |
| Temperature, °C. | 230–270 |
| Pressure, MPa Abs | 2.5–5.0 |
| Residence time @ HHL, min | 15–60 |
| Catalyst Concentration, wt % | |
| Clear wax draw | less than 0.2 wt % |
| Settler Bottoms | about 40 wt % |

There is no control valve for liquid flowing (203) from the reactor to the catalyst settling drum and there are no control valves on the clear liquid (204) overflow from the catalyst settling drum to the filters or on the catalyst concentrated slurry recycle (208) from the catalyst settling drum to the reactor. The underflow and overflow streams from the settling drum are pumped by variable speed positive displacement pumps and all flow indicators on these streams are venturi type meters. The flow rate through these pumps is controlled by the venturi flow meters which reset the speed of the pumps. By using these precautions, the chances of breaking up the catalyst and producing fines which are difficult to separate from the liquid are minimized.

The vapor steam leaving the reactor consists of unreacted CO and $H_2$ plus $CO_2$, water, methane, and hydrocarbon products lighter than the wax formed in the reactor. The reactor effluent stream is cooled (115) to 150° C. by heat exchange with boiler feed water and the resulting condensate is passed from flash drum (130) to the fractionator (140). Vapor from the flash drum (130) is cooled and vapor and liquid are separated in flash drum (135) where hydrocarbon liquids are passed to fractionator (140). The feedstreams to the fractionator (140) are fractionated by means known in the art with the fractionator overhead condensed in condenser (145). Product streams recovered by fractionation are as specified by design which may, as an example, include a $C_5$ product stream, a C6+ product stream, fractionator off gas stream and water and alcohols. Wax product is recovered from the catalyst settling separator (120).

This process invention works because of the unique skeletal iron catalyst that does not break down as easily as co-precipitated iron catalysts; therefore, the catalyst is readily separable from wax product by gravity settling.

Catalyst for the process comprises preferably a promoted skeletal iron catalyst of the composition as described herein. The catalyst is pretreated or activated as a slurry in hydrocarbon liquids by heating in vessel (105) in contact with hydrogen or nitrogen gas at elevated temperature between 320 to 350° C., for approximately one day. The pretreated catalyst is pumped to the (110) reactor bottom through conduit (210). The concentration of catalyst in the reactor slurry is preferably about 20 wt % with a particle size of 30–100 $\mu$ and a skeletal density in grams per cubic centimeter of about 7.9.

While a promoted catalyst composition is preferred for the skeletal iron catalyst particles used in the process of the invention, a skeletal iron catalyst without promoters may also be used.

Catalyst Preparation Process

The present invention provides preferably a promoted skeletal iron catalysts having unique composition for advantageous use in Fischer-Tropsch synthesis processes for CO and $H_2$ feedstreams for producing desired hydrocarbon liquid products. The promoted skeletal iron catalysts contain 70–90 wt % iron with the remainder being less than 10 wt % non-ferrous metal promoters of copper and manganese, and 0.1–3 wt % potassium, with the balance being aluminum. The promoted skeletal iron catalysts have surface areas in the range of 20–80 $m^2/g$, and preferably 30–65 $m^2/g$, and particle size range of 10–10,000 microns.

The catalyst preparation method steps for this invention includes first mixing iron chips/powder together uniformly with selected non-ferrous metal chips/powder, particularly aluminum, copper, and manganese in the proportion of 20–80 wt. % iron and 30–70 wt. % non-ferrous metals. A typical mixture may contain by weight 35–55% iron, 40–60% aluminum, 1–15% manganese and 0–10% copper. The metals uniform mixture is heated and melted to form a molten metal alloy, which is cooled rapidly to room temperature (15–20° C.) such as by quenching in water, and then pulverized to provide catalyst precursor particles having a 10–10,000 micron size range. The catalyst precursor particles are then extracted or leached by utilizing a suitable caustic solution such as 10–50% NaOH or KOH solution at 50–90° C. temperature for sufficient time such as 20–150 minutes to remove a major portion of aluminum from the iron alloy, and thereby form the base skeletal iron catalyst precursor material.

The resulting base skeletal iron catalyst precursor is next promoted with potassium by impregnating the potassium onto the base skeletal iron catalyst utilizing a suitable organic alcohol solution containing potassium, and then dried to evaporate the alcohol solvent and provide the promoted skeletal iron catalyst containing 0.1–3 wt. % potassium. Suitable alcohol solutions containing potassium may include but are not limited to methanolic potassium hydroxide, ethanolic potassium hydroxide, or potassium carbonate.

The dried promoted skeletal iron catalyst is next pretreated and/or activated such as by utilizing a hydrogen flow of 0.05–1.0 NL/g-cat/h in a fixed-bed reactor at a temperature of 300–350° C. for 2–12 hours to provide an active promoted skeletal iron catalyst, which can be then mixed with a suitable reaction medium such as liquid paraffin or ethanol and transferred into a reactor for use in F-T synthesis processes. Alternatively, the promoted skeletal iron catalyst can be activated or pretreated by mixing with a suitable reaction medium such as liquid paraffin to provide a slurry form, and then transferred directly into a slurry-phase F-T reactor and treated with hydrogen at a flow rate of 0.3–3.0 NL/g-cat/h and 300–350° C. temperature for 3–48 hours. The skeletal iron catalyst is then ready for effective use in catalytic F-T synthesis processes utilizing CO and $H_2$ feedstreams for producing desired hydrocarbon products. Nitrogen can also be used instead of hydrogen.

The final promoted skeletal iron catalyst particle size can be within a 10–10,000 micron range, with the larger particle size range of 1000–10,000 micron being for use in fixed bed reactors, and the smaller particle size range being 20–200 micron for use in slurry-phase reactors. The preparation of the catalyst is described in detail as follows Preparation of Catalyst Precursor Particles Mix together uniformly chips/powders of iron and non-ferrous metals selected from aluminum, copper and manganese to provide an iron content of 35–55 wt. %, 40–60 wt % non-ferrous metals and 5–15 wt. % manganese in the form of a carbonate compound. Heat and melt the uniformly mixed metals chips/powders in a suitable furnace such as an electric arc induction furnace to provide a molten metal alloy, and cool the molten alloy rapidly to room temperature (15–20° C.) by quenching in a suitable liquid such as water. Then mechanically pulverize the resulting solid metal alloy to provide iron alloy catalyst precursor particles having particle size range of 10–10,000 micron.

Preparation of Base Skeletal Iron Catalyst

The skeletal iron catalysts are prepared from the iron alloy catalyst precursor particles under an inert gas blanket by the following procedure:

Add a sufficient volume of caustic NaOH or KOH solution (10–50% concentration) into a stirred container, heat the solution to a temperature of 30–95° C., add the iron alloy particles (10–10,000 micron size) into the caustic solution, maintain the reaction condition for 2–150 minutes after the iron alloy particle addition is complete, and extract and/or leach out a major portion of the aluminum from the iron alloy particles. Then wash the treated iron alloy particles with deionized water to pH=7, replace the water with water-free ethanol, and temporarily store the resulting base skeletal iron catalyst particles in ethanol.

Impregnation of Potassium Promoter on the Base Skeletal Iron Catalyst

The impregnation of potassium promoter onto the base skeletal iron catalyst is performed as follows:

Prepare an alcohol solution containing a potassium compound such as a carbonate or nitrate having the desired potassium content based on the iron content in the catalyst, to provide potassium to iron weight ratio of 0.5–3:100. Transfer the base catalyst particles with alcohol solution to a rotating evaporator, then pour the required potassium solution into the same evaporator vessel, and vaporize the alcohol under controlled conditions of 40–80° C. temperature and 100–500 mm Hg vacuum pressure.

Activation of Promoted Skeletal Iron Catalyst

The promoted skeletal iron catalyst particles, after drying under vacuum, can be activated in either of the following ways before being used in an F-T reactor.

The dry catalyst particles are transferred into a fixed-bed activation reactor for activation with hydrogen, and then transferred to an F-T reactor, under inert gas protection while being transferred; the catalyst is then activated under a stream of hydrogen (0.05–1.0 NL/g-cat/hr) at a temperature of 300–350° for 2–12 hours.

After drying the impregnated catalyst particles, add sufficient liquid reaction medium such as liquid paraffin into the vessel to form a slurry, which is then transferred directly into the F-T reactor for in-situ activation using hydrogen (0.3–3.0 NL/g-cat/hr) at 300–350° for 3–48 hours.

General Synthesis Process Utilizing Promoted Skeletal Iron Catalyst

The promoted skeletal iron catalysts of this invention are uniquely useful in catalytic processes for Fischer-Tropsch synthesis of CO and $H_2$ feedstreams, particularly in slurry-phase reactors, to produce desired hydrocarbon products. Useful reaction conditions are $H_2$/CO molar ratio of 0.5–5:1 in the feedstreams and 5–40 wt. % catalyst loading relative to a reaction medium such as liquid paraffin, catalyst particle size of 1–10 mm (1000–10,000 microns) for fixed-bed reactors and 20–200 microns for slurry-phase reactors, 200–350° C. reaction temperature, 1.0–5.0 MPa system pressure, and gas hourly space velocity of 0.5–5 L/g-cat/h. A desired hydrocarbon liquid product containing used fine catalyst particles is withdrawn, and the fine catalyst particles are substantially removed from the liquid by gravitation settling of the particles.

The improved preparation methods for the promoted skeletal iron catalyst of this invention and its performance are further disclosed by the following examples, which should not be construed as limiting the scope of the invention.

EXAMPLE 1

1. Iron and aluminum chips are mixed together in respective weight ratio of 40:60, and heated in an electric-arc induction furnace under argon gas protection with constant stirring to form a uniform molten metal alloy. Then the molten iron-aluminum alloy is rapidly cooled to room temperature (15–20° C.) by quenching in water. The resulting solid metal alloy is mechanically pulverized to 0.1–3 mm (100–3,000 micron) particle size range to provide catalyst precursor particles.

2. Under hydrogen atmosphere, provide 25% concentration NaOH into a container and heat to 75° C. temperature, then slowly add alloy particles into the NaOH solution. Maintain this reaction condition for 90 minutes to extract or leach out a major portion of aluminum from the precursor iron alloy particles. Then wash the leached alloy particles with deionized water to pH approaches or equals 7, displace water with water-free ethanol and temporarily store the resulting catalyst particles in ethanol. Catalyst thus obtained has specific surface area 45 $m^2$/g, particle size 30–200 micron, and a composition of 72.9 wt % iron and 27.1 wt % aluminum.

3. Transfer the skeletal iron catalyst particles into a fixed-bed reactor and treat with hydrogen gas flow of 0.7 NL/g-cat/hr at 350° C. for 8 hours to activate the catalyst. Then under high-purity nitrogen gas protection, transfer the activated catalyst particles into a slurry-phase reaction medium for evaluation. The slurry-phase Fischer-Tropsch synthesis reaction conditions used for catalyst activity evaluation in a CO+$H_2$ feed stream include catalyst particle size of 0.044–0.074 mm (44–74 micron), catalyst loading of 15 wt %, relative to reaction medium, 0.7:1$H_2$/CO molar ratio, 270° C. temperature, and 2.5 Mpa pressure. Activity evaluation results for this skeletal iron catalyst compared with a reference precipitated iron catalyst under similar conditions are provided in Table 1.

EXAMPLE 2

1. Iron and aluminum chips are mixed uniformly with copper oxide and manganese carbonate ($MnCO_3$) in respective weight ratio of 38:58:2:2, and heated in an electric-arc induction furnace under argon gas protection with constant stirring to form a molten alloy. Then the molten iron-aluminum-copper-manganese alloy is rapidly cooled to room temperature (15–20° C.) by quenching in water. The resulting solid metal alloy is mechanically pulverized to 0.1–3 mm (100–3,000 micron) particle size range to provide promoted catalyst precursor particles.

2. Under hydrogen atmosphere, provide 25% concentration NaOH into a container and heat to 75° C. temperature, then slowly add the promoted catalyst precursor particles into the NaOH solution. Maintain this reaction condition for 90 minutes after the alloy addition to extract or leach out a major portion of aluminum from the promoted catalyst precursor particles. Then wash the leached alloy particles with deionized water to pH approaches or equals 7, displace water with water-free ethanol and temporarily store the resulting promoted catalyst particles in ethanol. The promoted catalyst obtained has a specific surface area of 54 $m^2$/g, particle size of 30–200 microns, a composition of 86.9 iron, 9.8 aluminum, 1.5 manganese, and 1.8 copper, all in wt %.

3. Transfer the promoted skeletal iron catalyst particles into a fixed-bed reactor and treat with hydrogen gas flow of 0.7 NL/g-cat/hr at 350° C. for 8 hours to activate the catalyst. Then under high-purity nitrogen gas protection, transfer the activated promoted catalyst particles into a slurry-phase reaction medium for evaluation. The slurry-phase Fischer-Tropsch synthesis reaction conditions used for catalyst activity evaluation in a CO+$H_2$ feed stream include catalyst particle size of 0.044–0.074 mm (44–74 micron), catalyst loading of 15 wt %, relative to reaction medium, 0.7:1 $H_2$/CO molar ratio, 270° C. temperature, and 2.5 Mpa pressure. Activity evaluation results for this promoted skeletal iron catalyst compared with a reference precipitated iron catalyst under similar conditions are provided in Table 1.

After the activity evaluation test is completed, the promoted skeletal iron catalyst and product wax slurry remained in the reactor is used for 15-minute gravity settling separation test, and test results are listed in Table 2.

EXAMPLE 3

1. Same as Step 1 in Example 2.
2. Under hydrogen atmosphere, provide 25% concentration NaOH into a container and heat to 75° C. temperature, then slowly add the catalyst precursor particles into the NaOH solution. Maintain this reaction condition for 90 minutes after the alloy addition to extract or leach out a major portion of aluminum from the alloy precursor particles. Then wash the leached alloy particles with deionized water to pH approaches or equals 7, displace water with water-free ethanol and temporarily store the resulting base catalyst particles in ethanol.

Next prepare a methanol solution of potassium carbonate and mix the leached catalyst particles with sufficient potassium solution to provide a potassium to iron weight ration in the catalyst of 2:100. Then gradually vaporize water and alcohol away under conditions of 200 mm Hg vacuum and 60° C. temperature to provide dry promoted skeletal iron catalyst particles. This dry catalyst has a specific surface area of 64 $m^2$/g, particle size of 30–200 micron; and a composition of 90.4 iron, 5.4 aluminum, 1.5 manganese, 1.8 copper, and 0.9 potassium, all in wt %.

3. Same as Step 3 in Example 2.

After catalyst activity evaluation is completed, 15-minute gravity settling test is conducted on the skeletal iron catalyst and product wax slurry that remained in the reactor. Test results are listed in Table 2. The test results are compared with similar 15-minute gravity settling test results of a reference precipitated iron catalyst, as shown in Table 3.

EXAMPLE 4

Catalyst preparation and activity evaluation of this example are the same as in Example 3. The difference is: iron and aluminum chips are mixed with copper oxide and manganese carbonate in respective weight ratio of 37:57:2:4.

The promoted skeletal iron catalyst thus obtained has a specific surface area of 58 $m^2$/g, particle size of 30–200 micron; and a composition of 90.6 iron, 3.5 aluminum, 1.9 manganese, 3.2 copper, and 0.8 potassium, all in wt %. Results of activity evaluation and catalyst/wax separation test are shown in Tables 1, 2 and 3.

EXAMPLE 5

1. Iron and aluminum chips are mixed uniformly with copper oxide and manganese carbonate in respective weight ratio of 35:55:3:7, and heated in an electric-arc induction furnace under argon gas protection with constant stirring to form a molten alloy. Then the molten iron-aluminum-copper-manganese alloy is rapidly cooled to room temperature (15–20° C.) by quenching in water. The resulting solid metal alloy is mechanically pulverized to 10–3,000 micron particle size range to provide promoted catalyst precursor particles.
2. Leaching of aluminum from alloy is conducted the same manner as in Step 2 of Example 3. The promoted skeletal iron catalyst thus obtained has a specific surface area of 61 $m^2$/g, 30–200 micron of particle size; a coposition of: 90.8 iron, 3.5 aluminum, 1.9 manganese, 2.3 copper, and 1.5 potassium, all in wt %.
3. Potassium loading is the same Step 3 of Example 3. The difference is that after loading is complete, mix promoted skeletal iron catalyst with liquid paraffin reaction medium to form a slurry for use in next step.
4. Transfer slurry prepared in last step into a Fischer-Tropsch reactor, and the promoted skeletal iron catalyst is treated with a hydrogen stream <1.0 NL/gcat/hr at 310° C. for 48 hours. After the treatment, CO+$H_2$ is fed to the reactor to start Fischer-Tropsch synthesis reaction with conditions: promoted skeletal catalyst particle size 0.044–0.074 mm, catalyst concentration in reaction medium 15 wt %, $H_2$/CO molar ratio of syngas 0.96:1, reaction temperature 270° C., reaction pressure 2.5 Mpa. Activity evaluation results of this promoted skeletal iron catalyst are presented in Table 1

EXAMPLE 6

1. Iron and aluminum chips are mixed uniformly with copper oxide and manganese carbonate in respective weight ratio of 37:57:3:3, and heated in electric-arc induction furnace under argon gas protection with constant stirring to form a molten alloy. Then the molten iron-aluminum-copper-manganese alloy is rapidly cooled to room temperature (15–20° C.) by quenching in water. The resulting solid metal alloy is mechanically pulverized to 10–3,000 micron particle size range to provide promoted catalyst precursor particles.
2. Leaching of aluminum from alloy to prepare base promoted skeletal iron catalyst is the same as Step 2 of Example 3.

3. Potassium loading step is the same as Step 3 of Example 3. Promoted skeletal iron catalyst thus obtained has 61 $m^2/g$ specific surface area, 30–200 micron particle size; and has a composition of 90.8 iron, 2.4 aluminum, 2.5 manganese, 2.8 copper, and 1.5 potassium, all in wt %.

Treatment and activity evaluation of this promoted skeletal iron catalyst are the same as corresponding steps of Example 3.

increased temperatures. Also with 100 vol. % hexane dilution of the catalyst/wax slurry, significant catalyst particle settling occurs at only 30° C. temperatures.

Catalyst/wax sedimentation for the promoted skeletal iron catalyst particle was further compared with a sample of precipitated iron catalyst at the various slurry temperatures for 15 minutes duration. The comparative test results are shown in Table 3.

TABLE 1

EVALUATION RESULTS OF PROMOTED SKELETAL IRON CATALYSTS

| Example No. | precipitated Iron* | 1 | 2 | 3 | 4 | 5 | 6 |
|---|---|---|---|---|---|---|---|
| Reaction Conditions | | | | | | | |
| Temperature, ° C. | 260 | 270 | 270 | 270 | 270 | 270 | 270 |
| Space Vel., NL/gcat-h | 1.8 | 1.5 | 3.0 | 3.0 | 2.0 | 2.0 | 2.0 |
| $H_2/CO$, mole. | 0.68 | 2.0 | 2.0 | 0.70 | 1.23 | 1.04 | 1.00 |
| Conversion, % | | | | | | | |
| CO | 81.0 | 74.7 | 77.7 | 82.5 | 68.9 | 76.8 | 88.4 |
| $H_2$ | 74.3 | 36.2 | 33.1 | 62.8 | 38.1 | 50.8 | 59.4 |
| Conv'd $H_2/CO$, mole. | 0.74 | 0.97 | 0.85 | 0.53 | 0.75 | 0.69 | 0.66 |
| Products, wt. % | | | | | | | |
| $C_1$–$C_2$, g/gFe-h | 0.019 | 0.032 | 0.052 | 0.052 | 0.043 | 0.025 | 0.048 |
| $C_3$–$C_4$. g/gFe-h | 0.023 | 0.040 | 0.072 | 0.079 | 0.052 | 0.034 | 0.053 |
| $C_5$+, g/gFe/h | 0.264 | 0.106 | 0.208 | 0.215 | 0.190 | 0.152 | 0.207 |
| $C_1$+, g/gFe-h | 0.306 | 0.178 | 0.332 | 0.346 | 0.285 | 0.211 | 0.308 |
| $CO_2$ (Conv'd CO) | 0.47 | 0.34 | 0.31 | 0.47 | 0.40 | 0.514 | 0.46 |
| $C_5$+ Simul. Distil. | | | | | | | |
| <177° C. | | 54 | 52 | 44 | 53 | 56 | 51 |
| 177–220° C. | | 13 | 14 | 17 | 13 | 10 | 14 |
| 220–360° C. | | 22 | 28 | 27 | 21 | 17 | 21 |
| >360° C. | | 11 | 6 | 12 | 13 | 17 | 14 |

*D. B. Bukar, X. Lang, Ind. Eng. Chem. Res. 1999, Vol. 38, 3270–3275.

Based on these results it is noted that the catalytic activity of the promoted skeletal iron catalyst is comparable to that of a precipitated iron catalyst.

After the catalyst evaluation tests were completed, the resulting product slurry material containing used skeletal iron catalyst particles and product wax was subjected to a catalyst/wax separation test by gravity sedimentation for 15 minutes duration at various temperatures. The catalyst separation results are shown in Table 2 below.

TABLE 2

CATALYST/WAX SEPARATION BY GRAVITY SEDIMENTATION

| Catalyst Separation Method | Product Slurry Temperature, ° C. | Catalyst remaining in clear wax, wt. % |
|---|---|---|
| Simple Sedimentation | 130 | 0.132 |
| | 185 | 0.085 |
| | 205 | 0.069 |
| Sedimentation with Hexane Dilution (1:1 in volume) | 30 | 0.096 |

The Table 2 results show that after 15 minutes sedimentation time, increased settling of the used skeletal iron catalyst particles in the wax slurry occurs at successively

TABLE 3

CATALYST/WAX SEPARATION BY GRAVITY SEDIMENTATION

| | Promoted Skeletal Iron Catalyst | Precipitated Iron Catalyst |
|---|---|---|
| Catalyst in Product Slurry, wt % | 15 | 3.0 |
| | Solid Concentration after Settling and (Efficiency), wt % | Solid Concentration after Settling and (Efficiency), wt % |
| Catalyst/Wax Slurry Temp., ° C. | | |
| 130 | 0.132(99.12) | 1.372(54.3) |
| 185 | 0.085(99.43) | 0.983(68.7) |
| 205 | 0.069(99.54) | 0.882(70.7) |

Based on the above catalyst/wax separation results, it is noted that although the concentration of catalyst solids in clear wax product is decreased at increased slurry temperatures for both the skeletal iron and the precipitated iron catalysts, the solid settling efficiencies i.e. the percentage of solids settled from the liquid wax after sedimentation compared to the original concentration, are significantly higher for the skeletal iron catalyst material.

The used promoted skeletal iron catalyst particle size distribution after 100 hour and 500 hour reaction times was also compared with that of fresh catalyst, with results being shown in Table 4 below.

TABLE 4

CATALYST PARTICLE SIZE DISTRIBUTION (WT %)

| Particle Size | Fresh Catalyst | Example 2 (After 100 hr Reaction) | Example 3 (After 500 hr Reaction) | Precipitated Iron (After 500 hr.) |
|---|---|---|---|---|
| 44–74 | 100 | 89.0 | 24.7 | 40 |
| 2.5–44 | 0 | 9.8 | 70.0 | 48 |
| <2.5 | 0 | 1.2 | 5.3 | 12 |

Table 4 results show that after the 100 hour and 500 hour periods of CSTR operations, the fresh promoted skeletal iron catalyst having initial 44–74 micron particle size range breaks down to smaller particles mostly in 2.5–44 micron range which are still easy to separate from wax slurry. When compared with the precipitated iron catalyst after 500 hour operation, the promoted skeletal iron catalyst had a desired lower percentage of particles smaller than 2.5 microns, which are most difficult to separate from wax.

What is claimed is:

1. A continuous catalytic process for the conversion of synthesis gas into hydrocarbon liquids and wax, including the separation of wax from catalyst particles by gravity sedimentation, comprising:
   contacting a feedstream comprising synthesis gas with a slurry of saturated hydrocarbon liquid arid skeletal iron catalyst particles in a reactor under conditions sufficient to convert the synthesis gas feedstream into by-product gases, light $C_1$–$C_4$ hydrocarbon gases, $C_5$+ hydrocarbon liquids and hydrocarbon wax,
      the skeletal iron catalyst particles having a skeletal structure formed by leaching a portion of metal from precursor particles;
   separating the by-product gases, light hydrocarbon gases and $C_5$+ hydrocarbon liquids, excluding wax, as a reactor vapor overhead stream for separation and recovery of $C_5$+ hydrocarbon liquid products;
   passing a reactor liquid slurry overflow stream rich in suspended skeletal iron catalyst particles and wax into a catalyst nettling drum through a reactor overflow line under conditions sufficient to separate catalyst particles and wax, wherein the skeletal iron catalyst particles in the overflow stream concentrate in a bottom portion of the drum by gravity sedimentation as a concentrated slurry of catalyst particles and hydrocarbon wax;
   withdrawing a catalyst settling drum side-draw stream essentially free of catalyst particles from an upper portion or the drum and recovering wax product therefrom; and
   passing a catalyst settling drum bottom stream rich in catalyst particles into a bottom portion of the reactor as a skeletal iron catalyst recycle stream.

2. The process of claim 1, further comprising:
   withdrawing a slip stream from the catalyst recycle stream as a spent catalyst purge stream; and
   adding fresh catalyst to the reactor.

3. The process of claim 1, further comprising:
   treating said reactor liquid slurry overflow stream rich in suspended skeletal iron catalyst particles and wax in a hydroclone before passing the treated stream to the catalyst settling drum whereby the separation of catalyst particles and wax is augmented.

4. The process of claim 1, wherein the reactor comprises a slurry bed reactor containing the skeletal iron catalyst particles.

5. The process of claim 4, wherein the reactor conditions comprise a temperature of 230–280° C. a pressure of 1.7–5.5 MPa, and a space velocity of 1.0–5.0 NL/g-cat/hr.

6. The process of claim 1, wherein the reactor further comprises internal cooling coils.

7. The reactor of claim 6, wherein a liquid level in the reactor is maintained above the tap of the cooling coils by a liquid overflow line.

8. The process of claim 1, further comprising:
   recovering product wax from the catalyst settling drum side-draw stream by pumping the side-draw stream through a filter to remove trace spent catalyst;
   passing the filtered stream to a wax product flash drum; and
   recovering clear wax product from a bottom portion of the flash drum.

9. The process of claim 1, wherein the catalyst settling drum side-draw stream contains less than 0.2 weight percent catalyst solids.

10. The process of claim 1, wherein skeletal iron catalyst particles are recycled to the reactor from the bottom of the catalyst settling drum by pumping the recycle stream to a position in the reactor below reactor cooling coils.

11. The process of claim 1, wherein the skeletal iron catalyst is an activated promoted catalyst.

12. The process of claim 11, wherein the catalyst is activated by heating in contact with hydrogen gas and/or nitrogen.

13. The process of claim 1, wherein the operating conditions of the catalyst settling drum comprise a temperature of 230–270° C., a pressure of 1.5–5.0 MPa Abs, and a residence time of 15–60 min.

14. The process of claim 1, wherein 90–99 weight percent of the suspended catalyst particles in the reactor overflow stream settle in the bottom portion of the catalyst settling drum.

15. The process of claim 1, wherein the syngas conversion comprises a once-through single pass operation.

16. The process of claim 1, wherein the syngas conversion comprises a recycle mode operation wherein unconverted hydrogen gas and carbon monoxide are recycled to the syngas conversion reactor.

17. The process of claim 4, wherein at least a portion of the skeletal iron catalyst particles in the slurry bed reactor have a particle size in a range of 20–200 microns.

18. The process of claim 1, wherein the reactor comprises a fixed bed reactor containing the skeletal iron catalyst particles, wherein the at least a portion of the skeletal iron catalyst particles in the fixed bed reactor have a particle size in a range of 1000–10,000 microns.

19. A continuous catalytic process for the conversion of synthesis gas into hydrocarbon liquids and wax, comprising:
   contacting synthesis gas with a slurry of hydrocarbon liquid and skeletal iron catalyst particles in a reactor under conditions sufficient to convert at least a portion of the synthesis gas into light $C_1$–$C_4$ hydrocarbon gases, $C_5$+ hydrocarbon liquids, hydrocarbon wax, and optionally by-product gases,
      the skeletal iron catalyst particles having a skeletal structure formed by leaching a portion of metal from precursor particles;

separating the light $C_1$–$C_4$ hydrocarbon gases, $C_5$+ hydrocarbon liquids, and any by-product gases from the hydrocarbon wax as a reactor vapor overhead stream;

passing a reactor liquid slurry overflow stream containing suspended skeletal iron catalyst particles and hydrocarbon wax into a catalyst settling drum;

concentrating the skeletal iron catalyst particles in the liquid slurry overflow stream in a bottom portion of the catalyst settling drum by gravity sedimentation as a concentrated slurry of catalyst particles and hydrocarbon wax;

withdrawing a catalyst settling drum side-draw stream essentially free of catalyst particles from an upper portion of the catalyst settling drum and recovering hydrocarbon wax product therefrom; and passing the concentrated slurry of catalyst particles and hydrocarbon wax into a bottom portion of the reactor as a skeletal iron catalyst recycle stream.

20. A continuous catalytic process for the conversion or synthesis gas into hydrocarbon liquids and wax, comprising:

forming synthesis gas comprised of carbon monoxide and hydrogen;

contacting the synthesis gas with a skeletal iron catalyst in a reactor under conditions sufficient to convert at least a portion of the synthesis gas into light $C_1$–$C_4$ hydrocarbon gases, $C_5$+ hydrocarbon liquids, hydrocarbon wax, and optionally by-product gases, the skeletal iron catalyst having a skeletal structure formed by leaching a portion of metal from precursor catalyst particles;

separating the light $C_1$–$C_4$ hydrocarbon gases, $C_5$+ hydrocarbon liquids, and any by-product gases from the hydrocarbon wax as a reactor vapor overhead stream;

passing a reactor liquid slurry overflow stream containing suspended skeletal iron catalyst and hydrocarbon wax into a catalyst settling drum;

concentrating the skeletal iron catalyst in the liquid slurry overflow stream in a bottom portion of the catalyst settling drum by gravity sedimentation as a concentrated slurry of the skeletal iron catalyst and hydrocarbon wax;

withdrawing a catalyst settling drum side-draw stream essentially free of the skeletal iron catalyst from an upper portion of the catalyst settling drum and recovering hydrocarbon wax product therefrom; and passing the concentrated slurry of the skeletal iron catalyst and hydrocarbon wax into a bottom portion of the reactor as a skeletal iron catalyst recycle stream.

* * * * *

UNITED STATES PATENT AND TRADEMARK OFFICE
CERTIFICATE OF CORRECTION

PATENT NO. : 6,903,141 B2
DATED : June 7, 2005
INVENTOR(S) : Zhou et al.

It is certified that error appears in the above-identified patent and that said Letters Patent is hereby corrected as shown below:

Column 5,
Line 16, change "slurryand" to -- slurry and --.
Line 46, change "vapor steam" to -- vapor stream --.

Column 7,
Line 9, after "as follows" insert -- : --.

Column 8,
Line 44, after "deionized water" change "to" to -- until --.

Column 9,
Lines 16 and 54, after "deionized water" change "to" to -- until --.
Line 40, change "remained" to -- remaining --.

Column 10,
Line 32, after "is conducted" insert -- in --.
Line 35, change "coposition" to -- composition --.

Column 13,
Table 4, line 14, after "(After 500 hr." insert -- ) --.

Column 15,
Line 19, change "conversion or" to -- conversion of --.

Signed and Sealed this

Twenty-first Day of February, 2006

JON W. DUDAS
*Director of the United States Patent and Trademark Office*